United States Patent
Rabe et al.

(10) Patent No.: US 11,083,880 B2
(45) Date of Patent: Aug. 10, 2021

(54) ANGLED CARTRIDGE ASSEMBLY FOR A DISPENSING DEVICE

(71) Applicant: The Procter & Gamble Company, Cincinnati, OH (US)

(72) Inventors: Thomas Elliot Rabe, Baltimore, MD (US); Faiz Feisal Sherman, Mason, OH (US); Stephan Gary Bush, Liberty Township, OH (US); Stephan James Andreas Meschkat, Bad Soden (DE); Grant Edward Anders Striemer, Cincinnati, OH (US); Andrea Colecchia, Agrate Brianza (IT); Simon Dodd, West Linn, OR (US)

(73) Assignee: The Procter & Gamble Company, Cincinnati, OH (US)

( * ) Notice: Subject to any disclaimer, the term of this patent is extended or adjusted under 35 U.S.C. 154(b) by 349 days.

(21) Appl. No.: 14/807,198

(22) Filed: Jul. 23, 2015

(65) Prior Publication Data
US 2016/0022972 A1    Jan. 28, 2016

Related U.S. Application Data

(60) Provisional application No. 62/028,935, filed on Jul. 25, 2014.

(51) Int. Cl.
*A61M 35/00* (2006.01)
*A45D 40/00* (2006.01)
(Continued)

(52) U.S. Cl.
CPC ........... *A61M 35/003* (2013.01); *A45D 34/00* (2013.01); *A45D 40/00* (2013.01); *A45D 40/26* (2013.01);
(Continued)

(58) Field of Classification Search
CPC ..... A61M 35/003; A45D 34/00; A45D 40/00; A45D 40/26; A45D 2034/005; A45D 2040/0006; A45D 2044/007; B05C 17/005
See application file for complete search history.

(56) References Cited

U.S. PATENT DOCUMENTS

| 3,323,641 A | 6/1967 | Landen |
| 5,160,315 A | 11/1992 | Heinecke |

(Continued)

FOREIGN PATENT DOCUMENTS

| AU | 2013200395 A1 | 3/2015 |
| EP | 2314245 A1 | 4/2011 |

(Continued)

OTHER PUBLICATIONS

Dictionary.com definition of "nozzle", www.dictionary.com/browse/nozzle.*
(Continued)

*Primary Examiner* — Tatyana Zalukaeva
*Assistant Examiner* — Jessica R Arble
(74) *Attorney, Agent, or Firm* — Melissa G Krasovec

(57) ABSTRACT

Included are embodiments of an angled cartridge assembly for modifying a treating surface. These embodiments may include a reservoir for storing a treatment composition, the treatment composition for being applied to the treating surface. Embodiments may also include a body portion that is coupled to the reservoir, where the body portion comprises a base surface and a dispensing surface, where the dispensing surface is disposed opposite the base surface on the angled cartridge assembly, and where the dispensing surface is disposed in a nonparallel configuration relative to the base surface.

6 Claims, 13 Drawing Sheets

(51) Int. Cl.
*A45D 34/00* (2006.01)
*A45D 40/26* (2006.01)
*B05C 17/005* (2006.01)
*H04N 7/18* (2006.01)
*A45D 44/00* (2006.01)

(52) U.S. Cl.
CPC ............ *B05C 17/005* (2013.01); *H04N 7/18* (2013.01); *A45D 2034/005* (2013.01); *A45D 2040/0006* (2013.01); *A45D 2044/007* (2013.01)

(56) References Cited

U.S. PATENT DOCUMENTS

| | | | |
|---|---|---|---|
| 5,308,180 A | 5/1994 | Pournoor et al. | |
| 5,614,310 A | 3/1997 | Delgado | |
| 6,139,829 A | 10/2000 | Estrin | |
| 6,312,124 B1 | 11/2001 | Desormeaux | |
| 6,347,868 B1* | 2/2002 | Headrick | B41J 3/36 347/109 |
| 6,386,692 B1 | 5/2002 | Cowger | |
| 6,461,467 B2 | 10/2002 | Blatchford | |
| 7,166,279 B2 | 1/2007 | Law | |
| 7,841,686 B2 | 11/2010 | Kyoshima | |
| 7,890,152 B2* | 2/2011 | Edgar | A45D 44/005 600/310 |
| 8,007,062 B2 | 8/2011 | Edgar | |
| 8,027,505 B2 | 9/2011 | Edgar | |
| 8,184,901 B2 | 5/2012 | Edgar | |
| 8,297,738 B1 | 10/2012 | Kodama et al. | |
| 8,695,610 B2 | 4/2014 | Samain | |
| 2003/0060810 A1 | 3/2003 | Syrowicz | |
| 2004/0078278 A1 | 4/2004 | Dauga | |
| 2004/0175347 A1 | 9/2004 | Bissett | |
| 2004/0186373 A1 | 9/2004 | Dunfield | |
| 2004/0230258 A1 | 11/2004 | Yaroslavsky | |
| 2005/0019510 A1* | 1/2005 | Gibson | B41J 2/1603 428/34.1 |
| 2006/0210513 A1 | 9/2006 | Luizzi | |
| 2006/0275237 A1 | 12/2006 | Bissett | |
| 2007/0035815 A1 | 2/2007 | Edgar | |
| 2007/0049832 A1 | 3/2007 | Edgar | |
| 2007/0148120 A1 | 6/2007 | Omura | |
| 2007/0224158 A1 | 9/2007 | Cassin | |
| 2008/0058783 A1 | 3/2008 | Altshuler | |
| 2008/0194971 A1 | 8/2008 | Edgar | |
| 2008/0317539 A1 | 12/2008 | Brugger | |
| 2009/0025747 A1* | 1/2009 | Edgar | A45D 44/005 132/320 |
| 2009/0131922 A1 | 5/2009 | Dewey | |
| 2010/0034574 A1* | 2/2010 | Zhang | A45D 40/24 401/47 |
| 2010/0224205 A1* | 9/2010 | Mitra | A61B 5/448 132/202 |
| 2010/0224211 A1 | 9/2010 | Rabe | |
| 2011/0129283 A1 | 6/2011 | Samain | |
| 2011/0155161 A1 | 6/2011 | Samain | |
| 2011/0159463 A1 | 6/2011 | Samain | |
| 2011/0162673 A1 | 7/2011 | Samain | |
| 2012/0056956 A1* | 3/2012 | Kodama | B41J 2/1752 347/86 |
| 2012/0113171 A1 | 5/2012 | Murata | |
| 2014/0163487 A1 | 6/2014 | Tout | |
| 2015/0237991 A1* | 8/2015 | Edgar | A45D 34/04 132/320 |
| 2015/0359315 A1 | 12/2015 | Rabe | |
| 2015/0359712 A1 | 12/2015 | Rabe | |
| 2015/0359714 A1 | 12/2015 | Rabe | |
| 2015/0360015 A1 | 12/2015 | Rabe | |
| 2015/0360016 A1 | 12/2015 | Rabe | |
| 2015/0360017 A1 | 12/2015 | Rabe | |
| 2016/0022006 A1 | 1/2016 | Rabe et al. | |
| 2016/0022008 A1 | 1/2016 | Rabe et al. | |
| 2016/0022009 A1 | 1/2016 | Rabe | |
| 2016/0022010 A1 | 1/2016 | Rabe | |
| 2016/0022011 A1 | 1/2016 | Rabe et al. | |
| 2016/0022972 A1 | 1/2016 | Rabe | |

FOREIGN PATENT DOCUMENTS

| | | |
|---|---|---|
| FR | 2933585 B1 | 10/2011 |
| GB | 2316657 A | 3/1998 |
| JP | 3101962 A | 4/1991 |
| JP | 9141846 A | 6/1997 |
| JP | 2001314226 | 11/2001 |
| JP | 2003054007 | 2/2003 |
| JP | 2006297691 A | 11/2006 |
| JP | 2007320066 A | 12/2007 |
| JP | 2010513091 A | 4/2010 |
| WO | WO2008/098234 A2 | 8/2008 |
| WO | WO2008/098235 A2 | 8/2008 |
| WO | WO2008/100878 A1 | 8/2008 |
| WO | WO2009/036876 | 3/2009 |
| WO | WO2010/004531 | 1/2010 |
| WO | WO2013/144186 A1 | 10/2013 |
| WO | WO2014028572 A2 | 2/2014 |

OTHER PUBLICATIONS

Bioresources Com et al: "Peer-Reviewed Article Novel Use of Waste Keratin and Cotton Linter Fibers for Prototype Tissue Papers and Their Evaluation", BioResources, Jul. 26, 2010 (Jul. 26, 2010), pp. 1425-1435.
ISR PCT/US2015/041887; Date of Mailing Dec. 15, 2015; 18 pages.
ISR PCT/US2015/041887; Date of Mailing Oct. 22, 2015; 7 pages.
ISR PCT/US2015/041888; Date of Mailing Nov. 5, 2015; 14 pages.
ISR PCT/US2015/041889; Date of Mailing Oct. 14, 2015; 12 pages.
ISR PCT/US2015/0418880; Date of Mailing Oct. 7, 2015; 12 pages.
ISR PCT/US2015/0418881; Date of Mailing Oct. 28, 2015; 12 pages.
ISR PCT/US2015/0418882; Date of Mailing Oct. 28, 2015; 11 pages.
U.S. Appl. No. 14/807,140, filed Jul. 23, 2015, Thomas Rabe.
U.S. Appl. No. 14/807,231, filed Jul. 23, 2015, Thomas Rabe.
U.S. Appl. No. 14/807,257, filed Jul. 23, 2015, Thomas Rabe.
U.S. Appl. No. 14/807,297, filed Jul. 23, 2015, Thomas Rabe.
U.S. Appl. No. 14/807,360, filed Jul. 23, 2015, Thomas Rabe.
Search Report and Written Opinion for PCT/US2015/041888 dated Nov. 5, 2015.
All Office Actions for U.S. Appl. No. 14/807,140, filed Jul. 23, 2015.
All Office Actions for U.S. Appl. No. 14/807,257, filed Jul. 23, 2015.
All Office Actions for U.S. Appl. No. 14/807,297, filed Jul. 23, 2015.
All Office Actions for U.S. Appl. No. 14/807,360, filed Jul. 23, 2015.
All Office Actions for U.S. Appl. No. 14/736,524, filed Sep. 14, 2015.
All Office Actions for U.S. Appl. No. 14/736,534, filed Jun. 11, 2015.
All Office Actions for U.S. Appl. No. 14/736,551, filed Jun. 11, 2015.
All Office Actions for U.S. Appl. No. 14/736,563, filed Jun. 11, 2015.
All Office Actions for U.S. Appl. No. 14/736,584, filed Jun. 11, 2015.
All Office Actions for U.S. Appl. No. 14/736,507, filed Jun. 11, 2015.
All Office Actions for U.S. Appl. No. 15/349,073, filed Nov. 11, 2016.

* cited by examiner

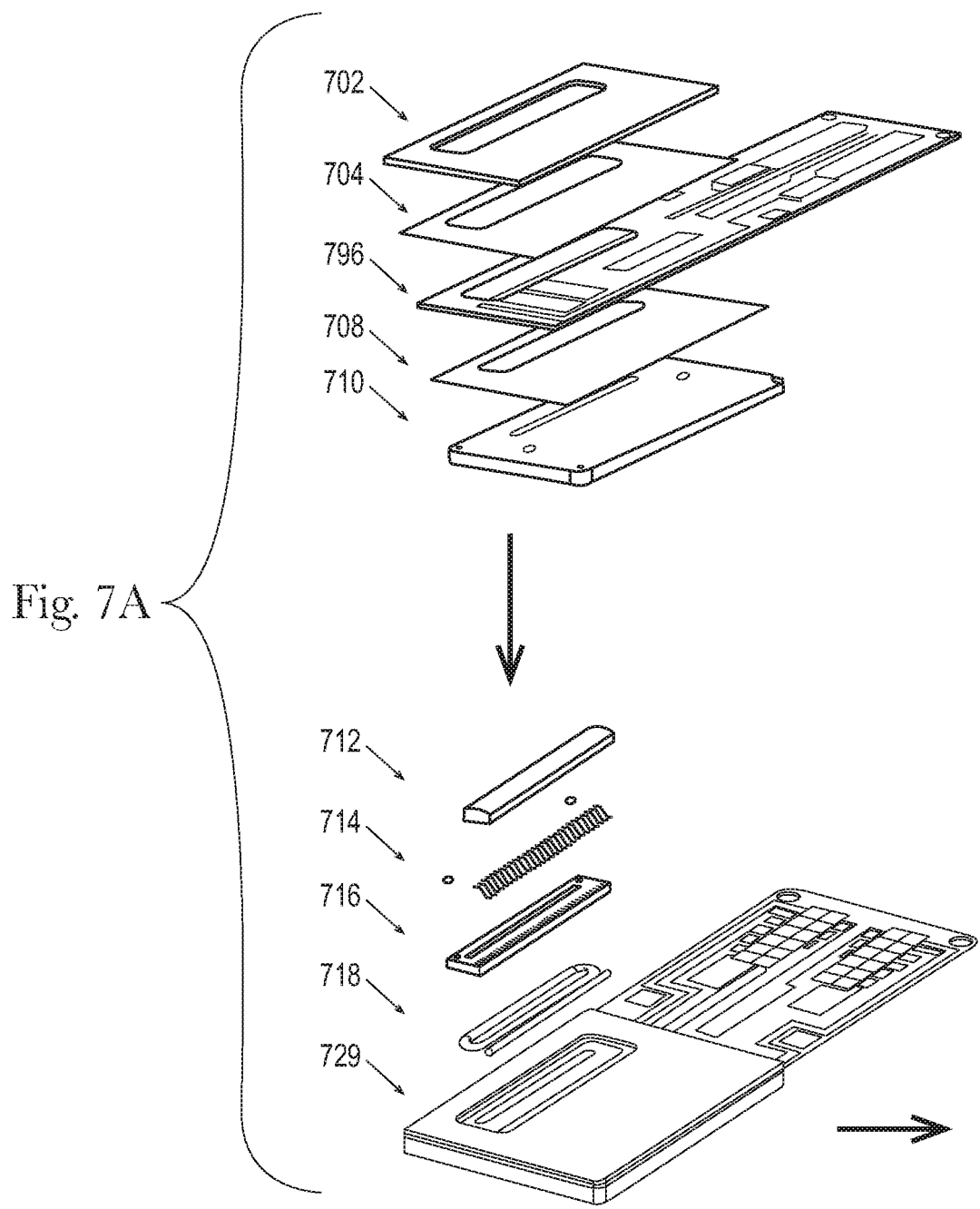

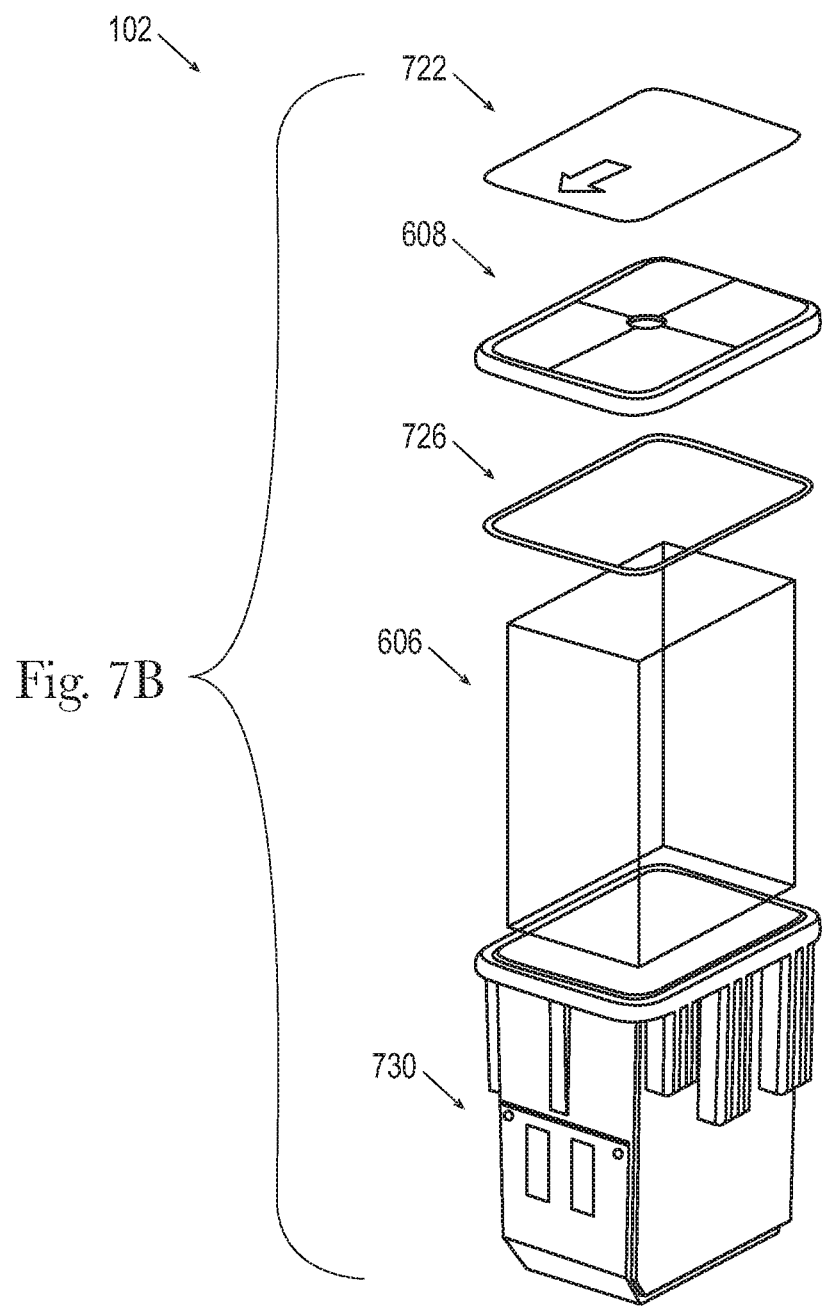

ANGLED CARTRIDGE ASSEMBLY FOR A DISPENSING DEVICE

FIELD OF THE INVENTION

The present application relates generally to a cartridge assembly for a dispensing device and specifically to an angled cartridge assembly that may be utilized in a device that modifies a keratinous surface or other treating surface.

BACKGROUND OF THE INVENTION

Tonal variations on human skin have multiple causes. Acne, freckles, sun damage, and age spots are just a few of the common causes of visible defects on skin. Textural variations such as fine lines, wrinkles and scars are also well known. Both tonal and textural deviations are highly noticeable to the human eye, even when they are quite small. Covering large areas of skin on and around deviations with makeup or other concealers is known.

Moreover, attempts have been made at more precise, and localized application of compositions that hide or cover-up skin deviations. Handheld devices that are moved across the skin have been developed to apply skin treatment compositions to local defects. But these devices have been plagued by the absence of speed and accuracy. For these handheld devices to work effectively, they must find the defects quickly, and treat them immediately. Finding a spot on the skin is of little use if the user has moved the applicator head to a different area of the skin before the spot can be effectively treated.

Accordingly, a need exists to treat this issue. A need further exists to provide a cartridge for such a device (and other types of dispensing devices) that provides and facilitates the needed functionality for the device.

SUMMARY OF THE INVENTION

Included are embodiments of an angled cartridge assembly for modifying a treating surface. These embodiments may include a reservoir for storing a treatment composition, the treatment composition configured for application to the treating surface. Embodiments may also include a body portion that is coupled to the reservoir, where the body portion comprises a base surface and a dispensing surface, where the dispensing surface is disposed opposite the base surface on the angled cartridge assembly, and where the dispensing surface is disposed in a nonparallel configuration relative to the base surface.

Also included are embodiments of a device for modifying a treating surface. Embodiments of the device may include an image capture device that, when the device is positioned in substantially perpendicular configuration relative to the treating surface, the image capture device is disposed at an image capture device angle that is neither parallel nor perpendicular to the treating surface. Embodiments may also include a cartridge assembly that is coupled to the image capture device. The cartridge assembly may include a base surface and a dispensing surface, where the dispensing surface is disposed opposite the base surface on the cartridge assembly, where when the device is positioned in substantially perpendicular configuration relative to the treating surface, at least a portion of the cartridge assembly is disposed at a cartridge assembly angle that is different than the image capture device angle, and where the cartridge assembly angle is neither parallel nor perpendicular to the treating surface when the device is positioned in substantially perpendicular configuration relative to the treating surface.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

FIGS. 7A, 7B depict components of the chip carrier and cartridge assembly according to embodiments disclosed herein.

DETAILED DESCRIPTION OF THE INVENTION

Embodiments disclosed herein include systems and methods for a cartridge assembly for a dispensing device. Accordingly, these embodiments may be configured to provide a locking key mechanism to ensure that the cartridge assembly is properly inserted into a cartridge housing. Additionally, embodiments may be configured with a blocking portion that further ensures proper insertion into the cartridge housing. The cartridge and cartridge assembly may be utilized in a device for treating a treating surface, such as a keratinous surface, skin, hair, nails, teeth, tongue, wood, metal, ceramic tile, fabric, tabletops, polymeric surfaces, paper, etc. In these embodiments, the cartridge assembly may include a reservoir for storing a treatment composition that is dispensed by the device onto the treating surface. As discussed herein, the treatment composition may include a paint, dye, cosmetic, medication, etc. In some embodiments, the treatment composition may be specifically configured for application to the human body, as identified by a proper regulatory body, such as the Food and Drug Administration or other governmental agency.

Figure 1:
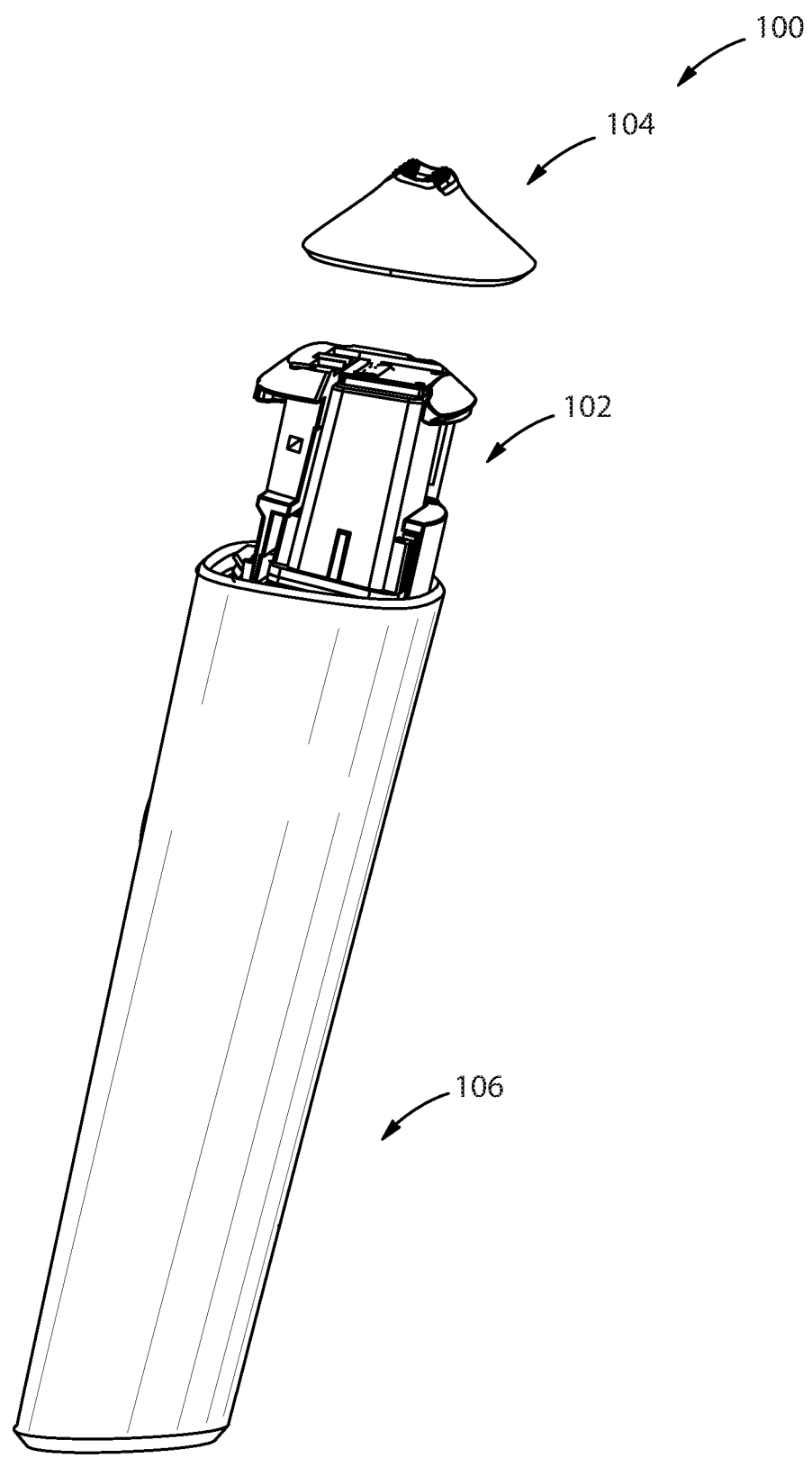
FIG. 1 depicts a perspective view of a device for modifying a treating surface that utilizes a cartridge assembly according to embodiments disclosed herein.

Referring now to the drawings, FIG. 1 depicts a perspective view of a device 100 for modifying a treating surface that utilizes a cartridge assembly 102, according to embodiments disclosed herein. As illustrated, the device 100 may include a spacer component 104 that may be utilized to provide a buffer between the treating surface (such as keratinous surface, skin, hair, nails, teeth, tongue, tabletops, wood, metals, tile, fabric, polymeric surfaces, paper, etc.) and the dispensing mechanisms of the device 100. Also provided is a handle portion 106, which may be configured to ergonomically reside in a user's hand, while also concealing one or more internal components of the device 100.

Similarly, the cartridge assembly 102 may be configured as a removably secured component that includes a reservoir for storing a treatment composition. The treatment composition may include an ink, a dye, a medication, a lotion, a paint, and/or other composition that will be applied to the treating surface. As described in more detail below, the cartridge assembly 102 may additionally include a die for dispensing the treatment composition to one or more nozzles (and/or a nozzle array) for applying the treatment composition to the treating surface.

Figure 2:
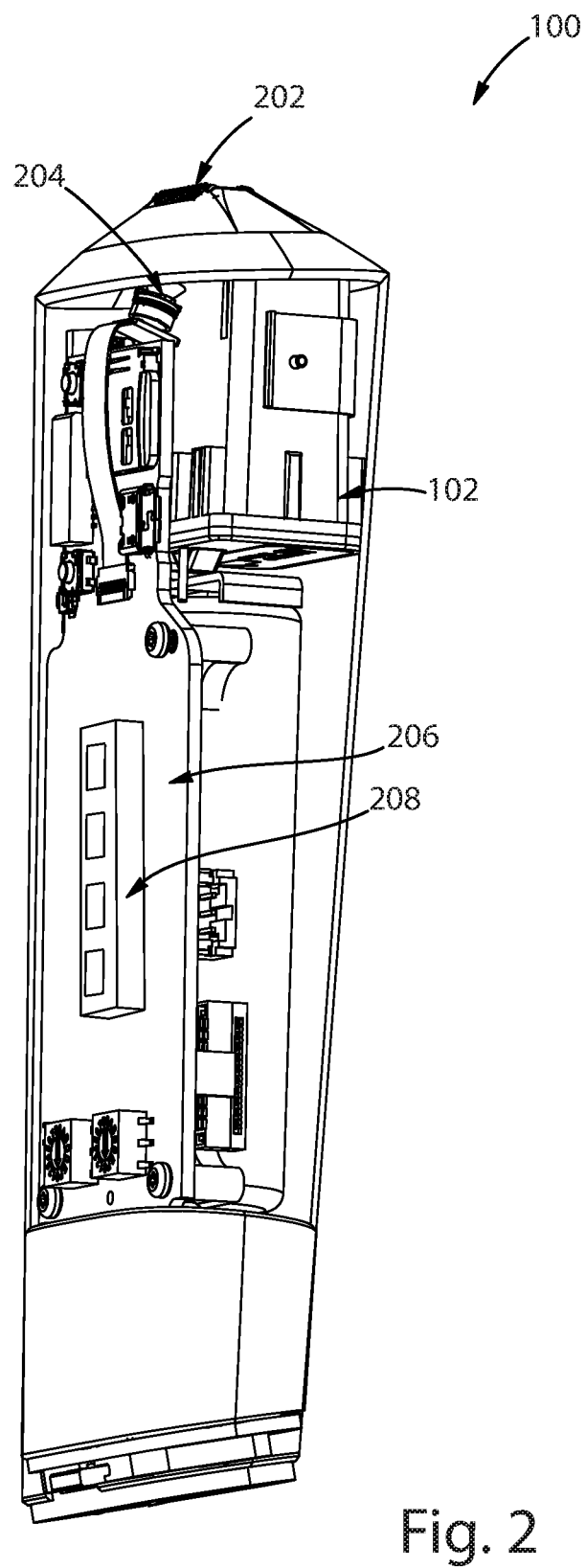
FIG. 2 depicts a perspective view of internal components of the device for modifying a treating surface, further illustrating the cartridge assembly according to embodiments disclosed herein.

FIG. 2 depicts a perspective view of internal components of the device 100 for modifying a treating surface, further illustrating the cartridge assembly 102, according to embodiments disclosed herein. As illustrated, the device 100 may include rollers 202 (one or more), an image capture device 204, the cartridge assembly 102, computing hardware 206, a display 208 (one or more), and/or other components. Specifically, the rollers 202 may be utilized as a lubricating mechanism for the device 100 when pressed against the treating surface. Specifically, as pressure is applied by the device 100 to the treating surface, it becomes more difficult for the device 100 to traverse along the treating surface. The rollers 202 may be utilized to alleviate this friction and allow the device 100 to more easily traverse the treating surface. The rollers are spaced apart from about 0.1 mm to about 10 mm, preferably from about 0.5 mm to about 6 mm and even more preferably from about 0.7 mm to about 4 mm. In alternative embodiments, the rollers may be coated to reduce friction (e.g. Teflon™, polyimide, parylene, etc.). The rollers may also be glides/gliding surfaces, sliding surfaces, balls, spheres, or flat or contain holes (i.e., like a mesh or screen) which may also be coated to reduce friction. The rollers can also be made of low friction materials like Teflon™.

Additionally, the device 100 includes an image capture device 204. The image capture device 204 may include an infrared sensor, a camera, a UV sensor, a spectrophotometer, and/or other similar device for providing the desired functionality. Specifically, the image capture device 204 may capture unwanted variations in the treating surface. The computing hardware 206, which may include a memory component, a processor, and logic. The computing hardware 206 may recognize the unwanted variation in the treating surface and may then send a command to the cartridge assembly 102 for dispensing the treatment composition. Also included are the display 208, which may provide indications regarding power, remaining battery life, status of nozzles, status of reservoir, and/or other information.

Figure 3:
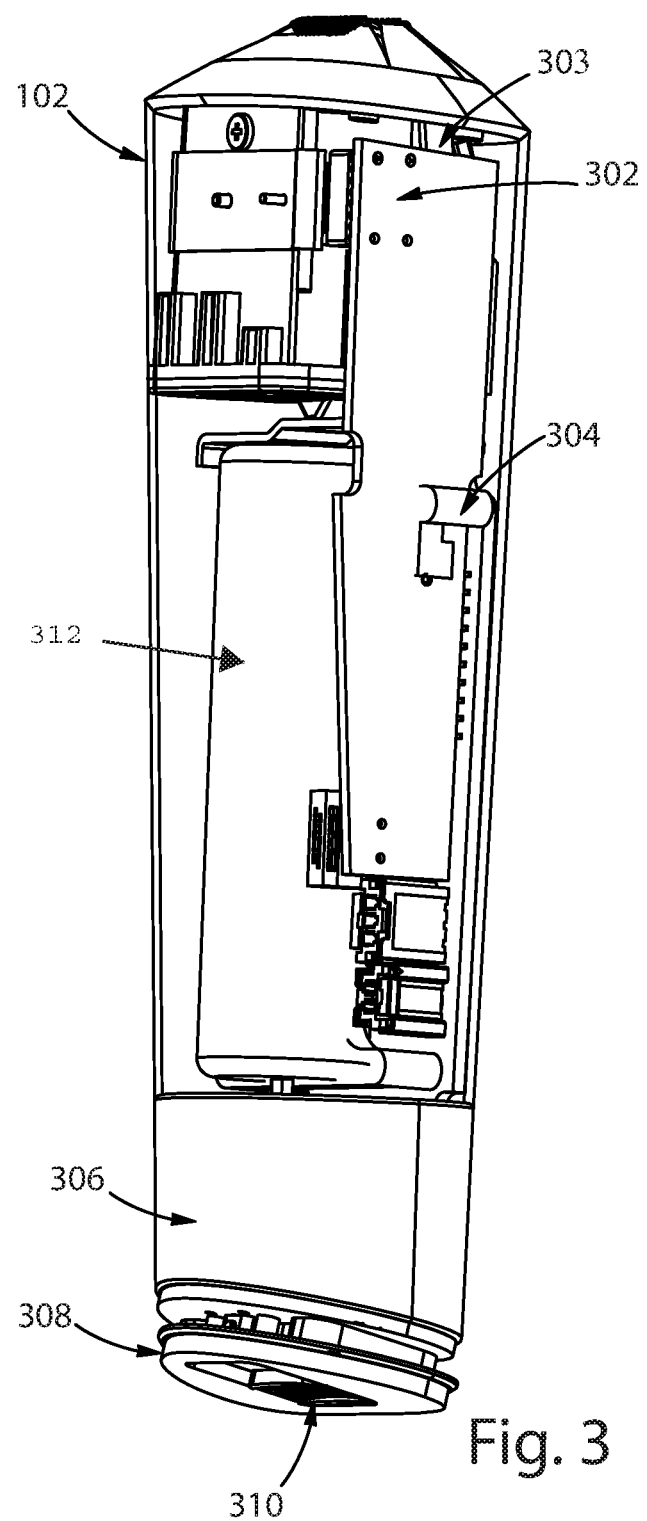
FIG. 3 depicts another perspective view of internal components of the device, further illustrating the cartridge assembly according to embodiments disclosed herein.

FIG. 3 depicts another perspective view of internal components of the device 100, further illustrating the cartridge assembly 102, according to embodiments disclosed herein. As illustrated, the cartridge assembly 102 is proximate to a pen driver 302, a bulge detector LED 304 and mirror 303, a tail illumination device 306, a power supply port 308, and a release mechanism 310, energy storage device 312, and wired or wireless connector 314. Mirror 303 may also be a prism, a diffraction grating or similar structure that bends light. Alternatively, a light guide (for example a fiber optic thread, wave guide, etc,) may be used to transport the light beam to the minor.

Specifically, the pen driver 302 may be configured to facilitate communication with the computing hardware 206 for implementing the nozzles. The nozzles can be in a linear array configuration, multiple rows, off-set rows, sine wave, curved, circular, or saw tooth arrangement. The bulge detector LED and minor 304 may be configured for detecting three dimensional variations in the treating surface (such as a bulge, dent, or other variation). The light source for 304 can be a light emitting diode (LED), incandescent light, neon bulb based or any other commercially available source of illumination. Light 304 can have constant illumination or adjustable illumination. The tail illumination device 306 may be configured to provide an aesthetic light source to the tail of the device 100. The power supply port 308 may be configured to couple with AC and/or DC power source for charging a battery of the device 100 (for battery powered embodiments). The release mechanism 310 may be utilized to release the device 100 from a charging dock or other similar external component. The energy storage device 312 may be a battery, a rechargeable battery, an electrochemical capacitor, a double-layer capacitor, a supercapacitor or a hybrid battery-capacitor system. The wired or wireless connector 314 provides communication between computing hardware 206 and external computing hardware of the internet, a user interface, or a display, via Bluetooth, WiFi, nearfield communication (NFC), RFID, etc.

Figure 4:
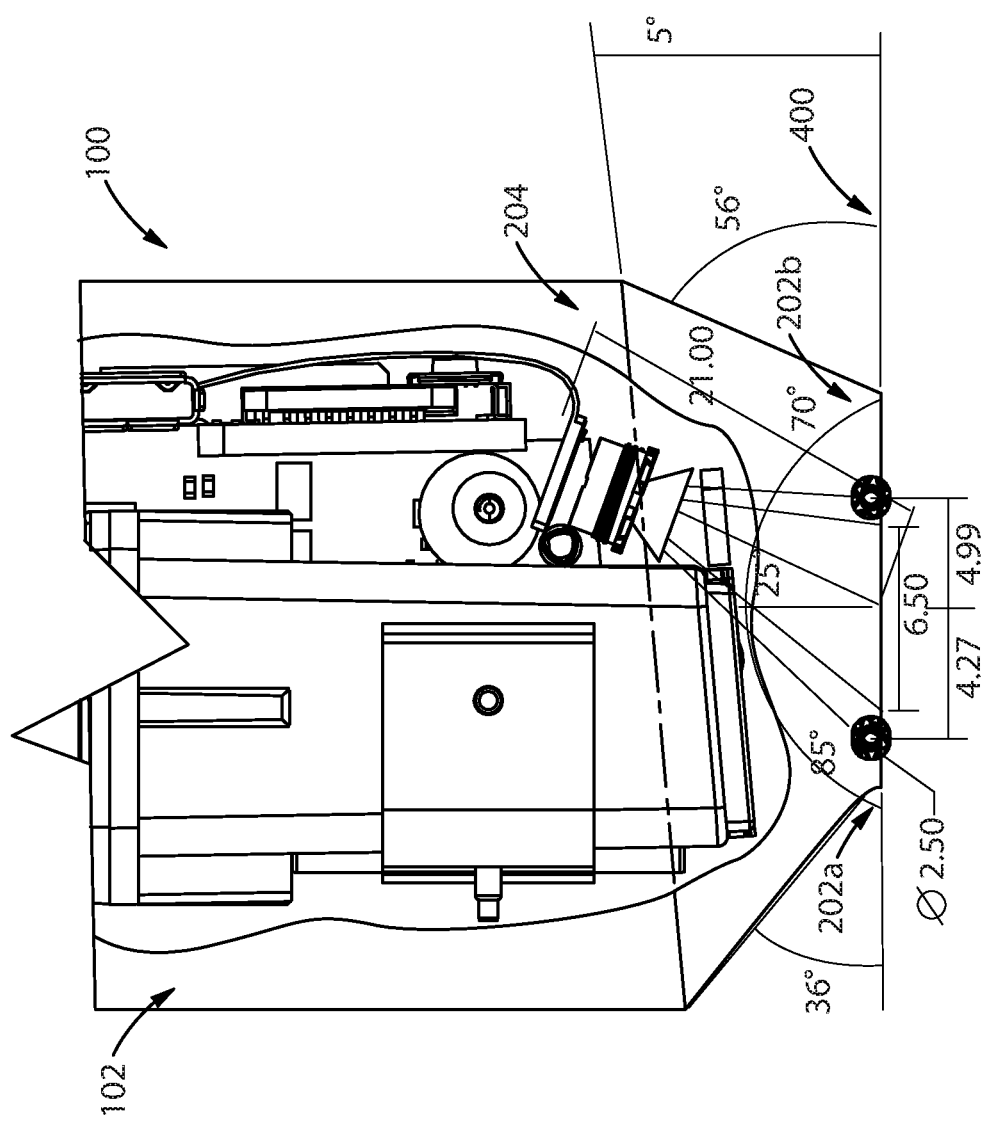
FIG. 4 depicts a side view of the device in operation with the cartridge assembly according to embodiments disclosed herein.

FIG. 4 depicts a side view of the device 100 in operation with the cartridge assembly 102 according to embodiments disclosed herein. As illustrated, the device 100 may be applied to a treating surface 400, such that the rollers 202a, 202b are pressed against the treating surface 400. As such, when the device 100 is disposed substantially parallel to the treating surface, the image capture device 204 may be disposed at an image capture device angle, such as about 70 degrees from the plane of the treating surface 400. Accordingly, the cartridge assembly 102 may be disposed at a cartridge assembly angle to accommodate for the image capture device 204. As illustrated, the cartridge assembly 102 may be disposed at an angle different than 90 degrees, relative to the treating surface 400. As discussed below, the cartridge assembly 102 may additionally have at least one side that is not 90 degrees relative to the other sides of the cartridge assembly 102. The nozzle may have about an 85 degree angle relative to the treating surface 400. Embodiments may have about a 25 degree angle between the image capture device 204 and nozzle center lines. Some embodiments may include about 6.5 mm by about 13 mm field of view. Additionally, some embodiments of the rollers 202 may be about 2.5 mm in diameter.

It should also be understood that when the device 100 is disposed substantially parallel to the treating surface 400, at least a portion of the cartridge assembly 102 may be disposed at an angle that is different than the angle of the image capture device 204 (e.g., the image capture angle is different than the cartridge assembly angle). Additionally, the at least a portion of the cartridge assembly 102 may be disposed at an angle that is neither parallel nor perpendicular to the treating surface 400.

Figure 5A:
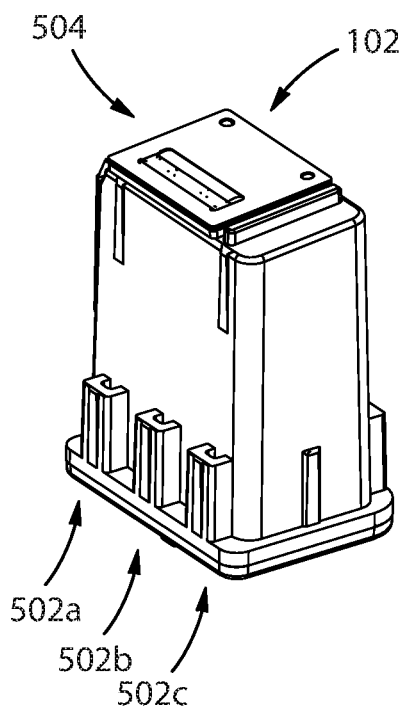
FIGS. 5A-5E depict a plurality of side views of the cartridge assembly according to embodiments disclosed herein.
Figure 5B:
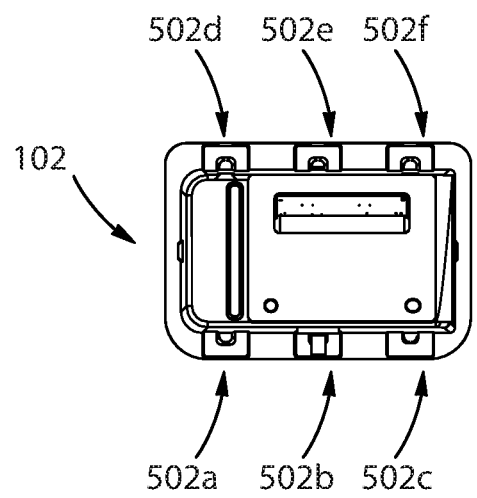

Thus in operation, the image capture device 204 may capture an image of an undesirable variation in the treating surface 400 illuminated by bulge detector LED and minor 304. The computing hardware 206 may calculate an amount of treatment composition to apply (and/or number of nozzle pulses) and a timing for applying the treatment composition to a desired area to strike that desired area. Computing hardware 206 may include Application Specific Integrated Circuit (ASIC), controller, Field Programmable Gate Array (FPGA), integrated circuit, microcontroller, microprocessor, processor, and the like. The computing hardware may also include memory functionality, either internal to the CPU as cache memory, embedded memory, Random Access Memory (RAM), Static Random Access Memory (SRAM) and the like or external to the CPU for example as Dynamic Random-Access Memory (DRAM), Read Only Memory (ROM), Static RAM, Flash Memory (e.g., Compact Flash or SmartMedia cards), disk drives, Solid State Disk Drives (SSD), embedded memory, or even Internet Cloud storage FIGS. 5A-5E depict a plurality of side views of the cartridge assembly 102 according to embodiments disclosed herein. As illustrated in FIG. 5A, the cartridge assembly 102 may include a plurality of engagement rails 502a, 502b, 502c, 502d, 502e, and 502f (collectively referred to as "engagement rails 502"), as well as a chip carrier assembly 504.

Included in the engagement rails 502 are primary engagement rails 502a, 502b, 502c, 502d, and 502e and auxiliary engagement rail 502f. Specifically, the primary engagement rails 502a-502e may be configured to couple with an interior portion of a cartridge housing in the device 100 to provide a sliding engagement therewith. The auxiliary engagement rail 502f may have a length that is shorter than the primary engagement rails 502a-502e, to facilitate proper insertion of the cartridge assembly 102 into the cartridge housing, as described in more detail below. In alternative designs, the sliding engagement can be a snap-on engagement or a combination of both.

Figure 5C:
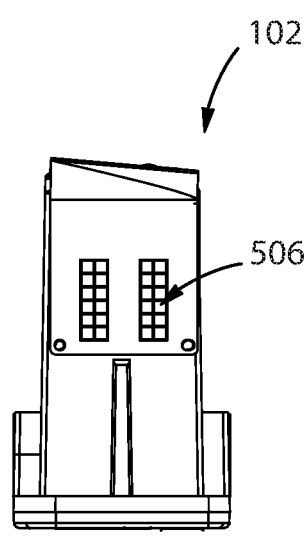
Figure 5D:
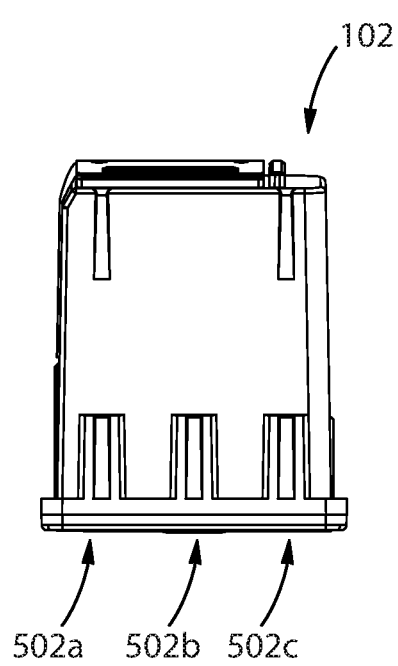

Additionally included is a connector 506, depicted in FIG. 5C. As illustrated in FIG. 5C, the connector 506 may include one or more electrical contacts, which provide a communicative connection with the computing hardware 206 (FIG. 2) for receiving instructions on dispensing the treatment composition from the chip carrier assembly 504 to the nozzles. Cleaning of the nozzles and other functionality may also be implemented via the connector 506. As an example, the cartridge assembly 102 may store information and the connector 506 may facilitate communication of that information to the device 100. Specifically, the connector 506 may communicate one or more of the following: contents of the treatment composition, logic for implementation on the device 100, an expiration date of the treatment composition, logic instructions for changing a setting on the device 100, etc. Connector 506 may also transmit electrical energy to provide power for energizing the nozzles.

Figure 5E:
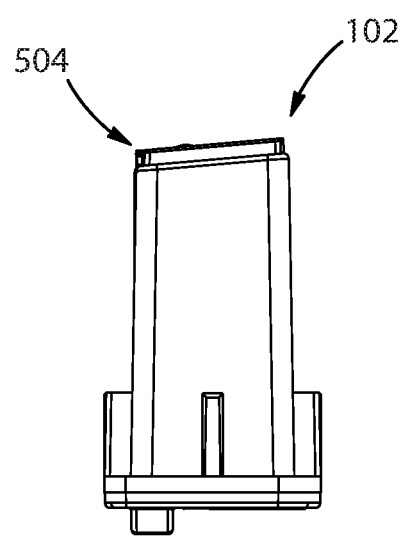

FIG. 5E illustrates that the cartridge assembly 102 may be configured with an angled orientation, providing an angled cartridge assembly. As discussed with regard to FIG. 4, the cartridge assembly 102 may be angled with regard to the treating surface 400. Accordingly, the cartridge assembly 102 may be shaped to accommodate this angled configuration. Specifically, the cartridge assembly 102 may include a base surface (depicted in FIG. 5E as the bottom surface) and a dispensing surface (depicted in FIG. 5E as the top surface) that is disposed at an angle that is different than 90 degrees from the other surfaces of the otherwise substantially rectangular cartridge assembly 102. The dispensing surface may be opposite the base surface and may be disposed in a nonparallel configuration relative to the base surface.

Additionally, some embodiments may be configured with a substantially rectangular body portion of the cartridge assembly 102, with the chip carrier assembly 504 having a carrier connection surface that is coupled to the body portion and a carrier dispensing surface opposite the carrier connection surface. In these embodiments, the carrier dispensing surface may be disposed in a nonparallel configuration relative to the carrier connection surface. In some embodiments, both the body portion and the chip carrier are angled in the described manner.

Figure 6A:
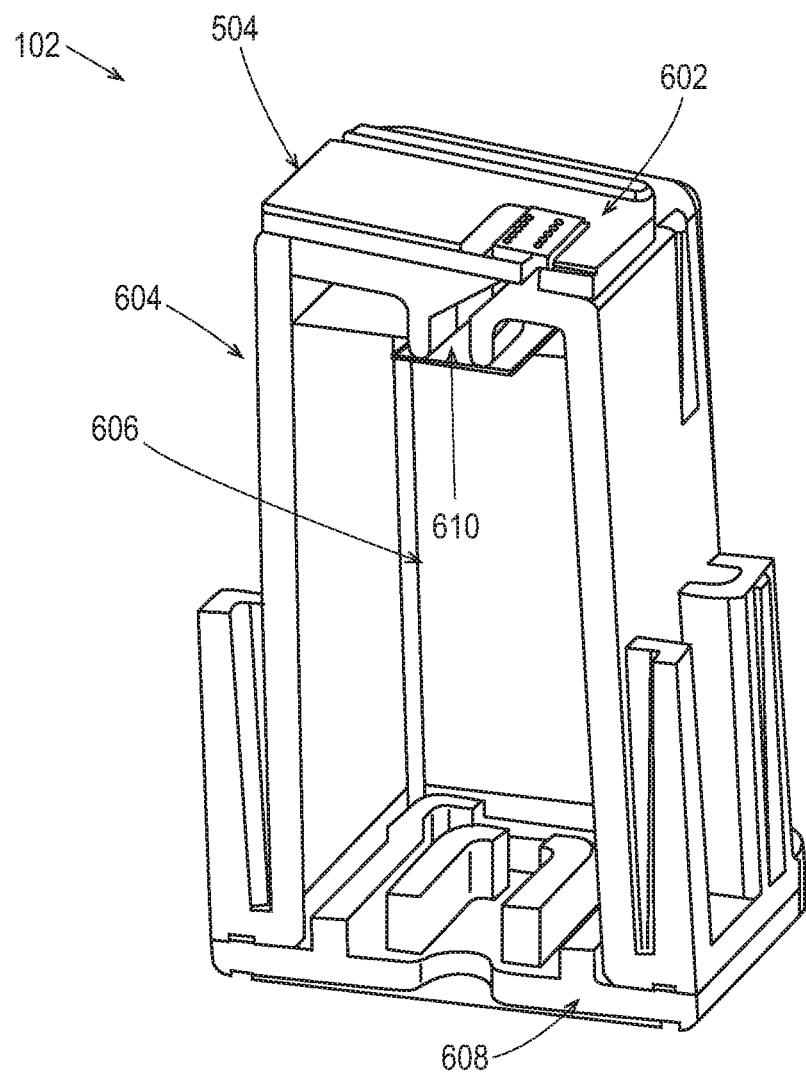
FIGS. 6A, 6B depict a plurality of perspective views of the cartridge assembly illustrating a plurality of internal components, according to embodiments disclosed herein.
Figure 6B:
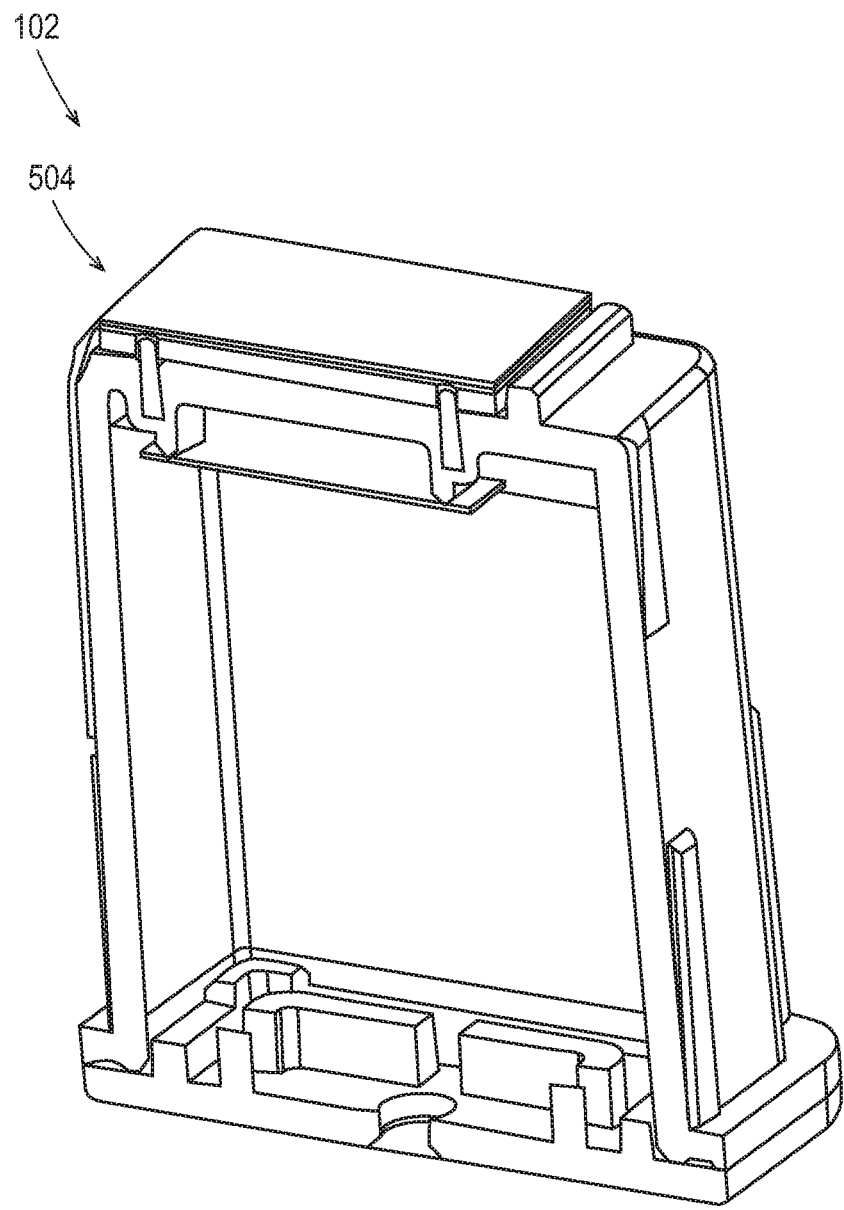

FIGS. 6A, 6B depict a plurality of perspective views of the cartridge assembly 102 illustrating a plurality of internal components, according to embodiments disclosed herein. Specifically, the cartridge assembly 102 includes the chip carrier assembly 504, which includes a die 602. Die 602 may be configured from substrates, printed circuit boards, silicon, glass, machineable glass ceramic, sapphire, alumina, Liquid Crystal Polymer, polyimide and MEMS (MicroElectroMechanical Systems) devices. The cartridge assembly 102 also includes a reservoir 604 for storing the treatment composition. The reservoir 604 may be lined with foam 606 and/or other similar material. Also included is a plug 608 for sealing, filling, and/or draining the reservoir 604. The reservoir 604 is in communication with the chip carrier assembly 504 and the nozzles.

Also depicted in FIG. 6A is an opening 610 in the reservoir 604 for dispensing the treatment composition via the die 602. While a pump mechanism may be utilized for dispensing the treatment composition, some embodiments utilize gravity and position the cartridge assembly 102 in an inverted position, which allows the treatment composition to naturally flow to the die 602. FIG. 6B further depicts the cartridge assembly 102 and die 602 from a different perspective. Thermal ink jet, and piezoelectric ink jet may be utilized for dispensing the treatment composition through die 602.

FIGS. 7A, 7B depict components of the chip carrier assembly 504 and cartridge assembly 102 according to embodiments disclosed herein. As illustrated in FIG. 7A, the chip carrier assembly 504 includes a plurality of layers 702, 704, 796, 708, 710, which may be configured as substrates, printed circuit boards, silicon, glass, machineable glass ceramic, sapphire, alumina, Liquid Crystal Polymer, polyimide, and MEMS (MicroElectroMechanical Systems) devices. and/or other components, which may be flexible, rigid flex, and/or rigid. The chip carrier assembly 504 may additionally include the die 602, which may include a plurality of components 712, 714, 716, 718, 729. These components may be secured to the chip carrier assembly 504 and facilitate dispensment of the treatment composition onto the treating surface 400 (FIG. 4).

Figure 8A:
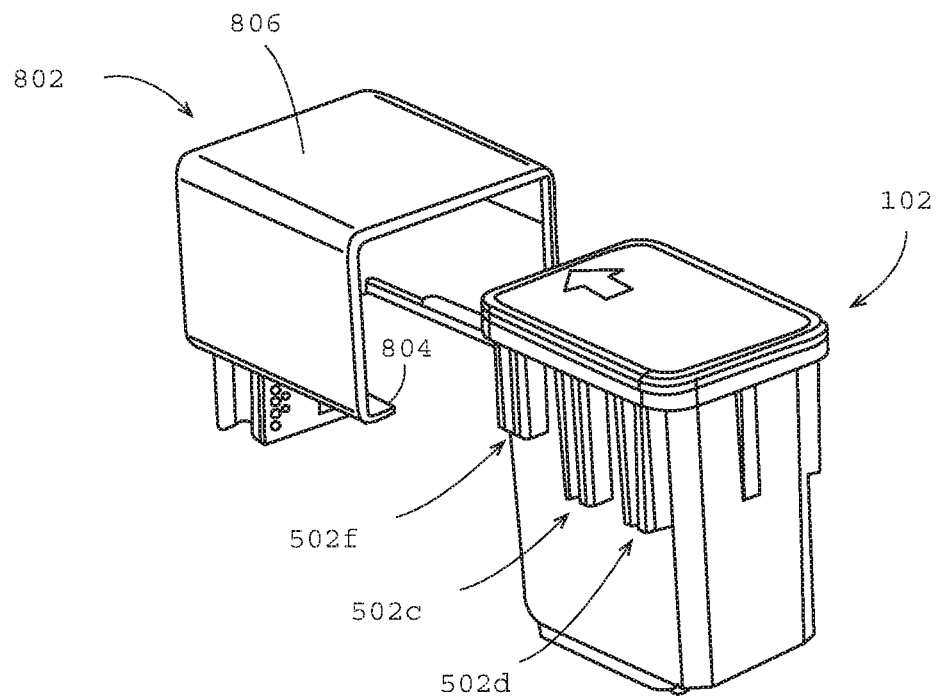
FIGS. 8A-8E depict interaction of the cartridge with a cartridge housing, according to embodiments disclosed herein.

FIG. 7B depicts the cartridge assembly 102, which may include a visual cue 722 for indicating a proper direction for insertion of the cartridge assembly 102 into a cartridge housing. The visual cue 722 may include a printed label, an engraving and/or other signifier of a direction for inserting the cartridge assembly 102 into the cartridge housing. A plug 608 may also be included, as well as a washer 726, the foam 606, and the body portion 730. The components of FIG. 7B may be assembled and coupled to the assembly from FIG. 7A to form the cartridge assembly 102. Visual cue 722 can also be placed on the cartridge assembly 802 or handle portion 106.FIGS. 8A-8E depict interaction of the cartridge assembly 102 with a cartridge housing 802, according to embodiments disclosed herein. As illustrated in FIG. 8A, the cartridge assembly 102 may be configured for insertion into the cartridge housing 802. In order to ensure full insertion of the cartridge assembly 102 into the cartridge housing, the cartridge assembly 102 may include the primary engagement rails 502a-502e, as well as the auxiliary engagement rail 502f. The cartridge housing 802 may include a securing rail 804 that is a predetermined length from a top portion 806 of the cartridge housing 802. The length between the securing rail and the top portion 806 may substantially correspond with a length of the primary engagement rails 502a-502e (as measured from a top portion 806 of the cartridge assembly 102) to allow for insertion of the cartridge assembly 102 into the cartridge housing 808. Additionally, the cartridge housing 802 may include a blocking component 810 (FIG. 8C) that extends from the securing rail 804 towards the top portion 806 of the cartridge housing 802. This blocking component 810 is arranged to allow the cartridge assembly 102 to be fully inserted into the cartridge housing 802 when properly aligned because the auxiliary engagement rail 502f has a length that is shorter than the length of the primary engagement rails 502a-502e, allowing the cartridge assembly 102 to pass the blocking component 810 when inserted into the cartridge housing 802.

Figure 8B:
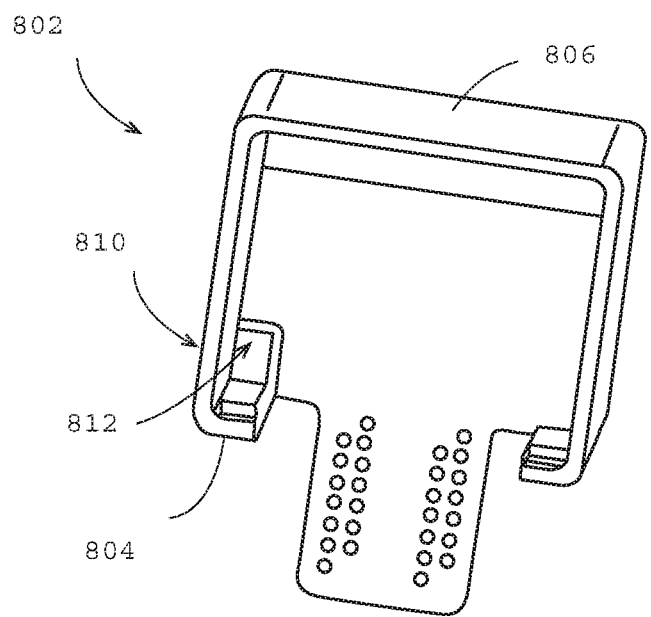

Depicted in FIG. 8B is a locking key mechanism 812, which engages the auxiliary engagement rail 502f to ensure that the cartridge assembly 102 is properly inserted into the cartridge housing 802. Specifically, the locking key mechanism 812 may be configured to receive an electronic or physical marker from the cartridge assembly 102. If the marker is incorrect or missing, the cartridge housing 802 will indicate that the cartridge assembly 102 is not properly inserted. Locking key mechanism may include a software lock using software codes to lock or unlock the cartridge assembly. The locking features can also be used to determine if counterfeit material or cartridges are being used.

Figure 8C:
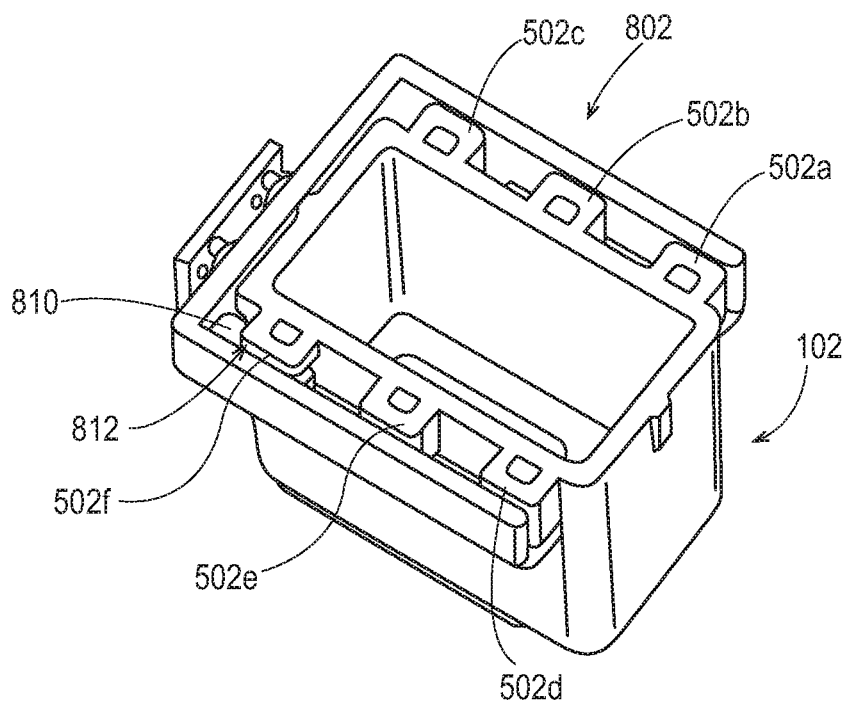

As illustrated in FIG. 8C, the cartridge assembly 102 has been properly inserted in to the cartridge housing 802. Accordingly, the auxiliary engagement rail 502f passes by the blocking component 810 to engage with the locking key mechanism 812.

Figure 8D:
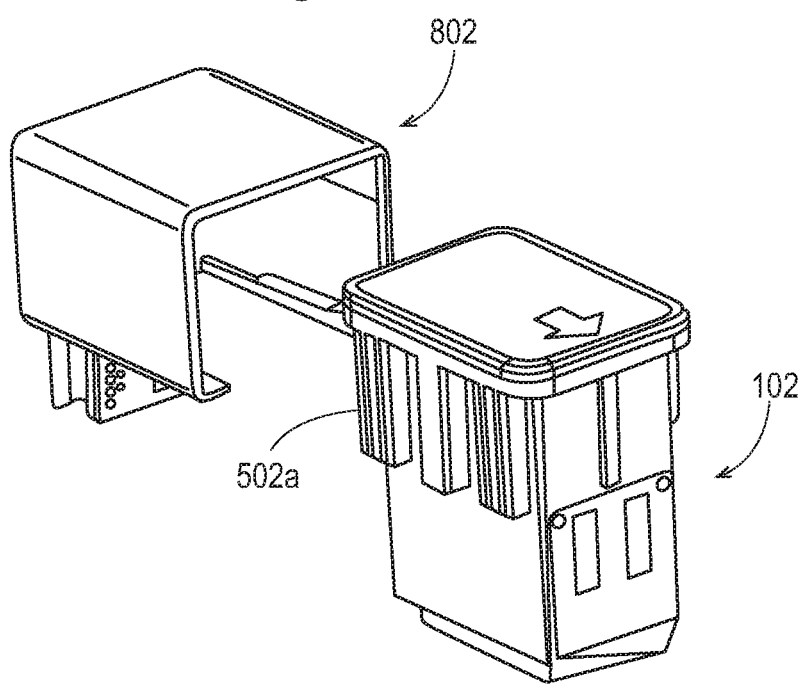
Figure 8E:
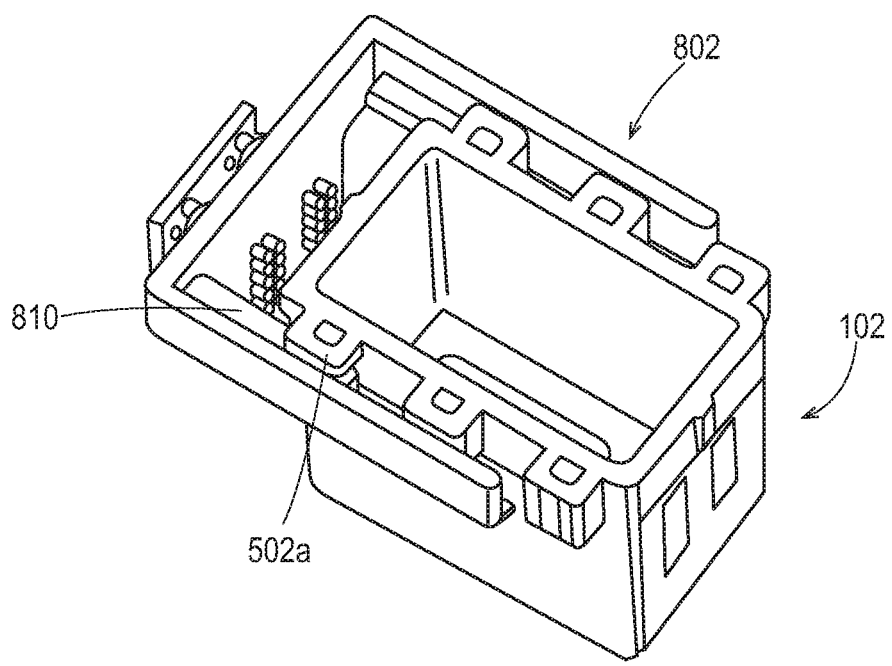

FIG. 8D illustrates that the cartridge assembly 102 being improperly inserted into the cartridge housing 802. As a consequence, the primary engagement rail 502a will contact the blocking component 810, which prevents full insertion into the cartridge housing 802. Additionally, the locking key mechanism 812 will not receive the marker from the cartridge assembly 102 to verify that the cartridge assembly 102 is properly inserted. This is illustrated in FIG. 8E, where the primary engagement rail 502a contacts the blocking component 810.

It should be understood that while some embodiments utilize the primary engagement rail 502a-502e and the auxiliary engagement rail 502f, this is merely an example. Some embodiments may utilize a primary engagement portion (one or more) and an auxiliary engagement portion (one or more) that extends from a surface of the cartridge assembly 102 and provides similar function as the engagement rails 502. These engagement portions may not be shaped as depicted in the drawings herein, but instead may be shaped as notches that extend from a surface of the cartridge assembly 102 and serve a similar function as the engagement rails 502. Accordingly, the auxiliary engagement portion may be positioned closer to a first end of the cartridge assembly 102 (which may include an opposing first end and second end) than the primary engagement portion. This allows the cartridge assembly 102 to pass the blocking component for full insertion into the cartridge housing 802.

It should also be understood that while the cartridge assembly 102 and cartridge housing 802 are depicted as residing in the device 100, this is also an example. Other devices for dispensing a treating composition may utilize the cartridge assembly 102 and/or cartridge housing 802 as described herein.

Additionally, some embodiments may be configured to utilize the angled dispensing surface for providing an authentication between the cartridge assembly 102 and the cartridge housing 802. Specifically, the cartridge housing 802 may be similarly shaped with the top portion 806 being similarly angled to accommodate the cartridge assembly 102. Similarly, some embodiments may include an additional securing rail on the cartridge housing 802 to prevent insertion of non-angled cartridges into the cartridge housing 802.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:

1. A device for modifying a treating surface, comprising:
an image capture device for capturing an image of the treating surface;
a cartridge housing that is shaped to removably secure a cartridge assembly to the device, the cartridge assembly comprising a reservoir for storing a treatment composition and a body portion that is coupled to the reservoir, wherein the body portion comprises a base surface and a dispensing surface comprising an array of nozzles for applying the treatment composition to the treating surface, wherein the dispensing surface is disposed opposite the base surface on the cartridge assembly; wherein a center line of the image capture device is neither parallel nor perpendicular to a center line of the array of nozzles; and
a removable spacer component configured to provide a buffer to the dispensing surface, wherein the spacer component comprises an opening.

2. The device of claim 1, wherein the cartridge assembly comprises a chip carrier assembly that facilitates dispensing a treatment composition onto the treating surface.

3. The device of claim 1, wherein the treatment composition is a cosmetic.

4. The device of claim 1 further comprising a processor, wherein the cartridge assembly further comprises a connector for communicatively coupling the cartridge assembly and the processor for controlling dispensing of a treatment composition, wherein the connector facilitates communication of information related to the cartridge assembly to the device, and wherein the information includes at least one of the following:

contents of the treatment composition, logic for implementation on the device, an expiration date of the treatment composition, logic instructions for changing a setting on the device, or remaining battery life.

5. The device of claim 1, wherein the treatment surface is skin.

6. The device of claim 1, wherein the center line of the image capture device and the center line of the array of nozzles pass through the opening.

* * * * *